United States Patent [19]
Meyer

[11] Patent Number: 6,053,892
[45] Date of Patent: Apr. 25, 2000

[54] SYRINGE HEAD WITH WARRANTY SEAL

[75] Inventor: Philippe Meyer, Zürich, Switzerland

[73] Assignee: Becton Dickinson France S.A., Le Pont-de-Claix, France

[21] Appl. No.: 09/202,892

[22] PCT Filed: Jun. 24, 1997

[86] PCT No.: PCT/EP97/03296

§ 371 Date: Dec. 22, 1998

§ 102(e) Date: Dec. 22, 1998

[87] PCT Pub. No.: WO97/49444

PCT Pub. Date: Dec. 31, 1997

[30] Foreign Application Priority Data

Jun. 25, 1996 [AT] Austria ................................. 1122/96

[51] Int. Cl.$^7$ ........................................ A61M 5/00
[52] U.S. Cl. ....................... 604/110; 604/111; 604/218
[58] Field of Search .................................. 604/218, 110, 604/187, 192, 263, 111

[56] References Cited

U.S. PATENT DOCUMENTS 3,333,682 8/1967 Burke .
4,820,275 4/1989 Haber et al. .
5,250,037 10/1993 Bitdinger .

FOREIGN PATENT DOCUMENTS

WO 86 03126 6/1986 WIPO .
WO 94 22511 10/1994 WIPO .

Primary Examiner—John D. Yasko
Attorney, Agent, or Firm—Frishauf, Holtz, Goodman, Langer & Chick, P.C.

[57] ABSTRACT

A hypodermic syringe head with tamper-evident closure for a syringe barrel, having an injection cannula (4) which is mounted in a cannula carrier (5) from which it protrudes on both axial ends and which is disposed in a cannula carrier guide, so as to be movable relative thereto, and a cannula guard cap (1), which is adjoined via a rated breaking point (2) by an anchoring element (3) that solidly holds the cannula carrier guide and can be affixed to the barrel neck, wherein a sealing disk (7) is received in the anchoring element, and two axially symmetrical guide grooves (15) for a guide peg (16) of the cannula carrier guide are embodied on the circumference of the cannula carrier, the guide grooves extending at a predetermined inclination substantially to form a V and opening into one another on their end toward the sealing disk, and in the unactuated state of the hypodermic syringe head, the guide peg engages the orifice region (15') of the guide grooves that is oriented toward the sealing disk, and upon a rotation of the cannula guard cap (1) in each of the two directions of rotation, the guide peg slides relative to one of the two guide grooves, destroying the rated breaking point.

8 Claims, 3 Drawing Sheets

SYRINGE HEAD WITH WARRANTY SEAL

BACKGROUND OF THE INVENTION

1. Field of the Invention

The invention relates to a hypodermic syringe head with a tamper-evident closure for a syringe barrel, which has a barrel neck that is provided with an axial fluid outlet conduit and a circumferential bead for anchoring the hypodermic syringe head, having an injection cannula, which is mounted in a cannula carrier from which it protrudes on both axial ends and which is disposed in a cannula carrier guide so as to be movable relative thereto, and a cannula guard cap which is adjoined, via a rated breaking point, by an anchoring element that solidly holds the cannula carrier guide and can be affixed with elastic deformation to the circumferential bead of the barrel neck, and the cannula guard cap has axially extending ribs on its inside circumference which engage corresponding ribs of the cannula carrier for rotationally driving it.

2. Description of the Prior Art

One such hypodermic syringe head is intended to close so-called ready-to-use syringes, that is, syringes that are filled with a liquid medication and packed in sterile form, with an injection cannula, and are sold ready for use. It is understood that these ready-to-use syringes are provided with a tamper-evident closure, which makes it possible to see whether the syringe is still filled with the original contents and is still sterile. The hypodermic syringe head is intended to protect the cannula adequately so that upon final mounting of the syringe head on the syringe barrel, no damage to or contamination of the cannula can occur. For the sake of mass production, a simple construction of the hypodermic syringe is also necessary.

In one hypodermic syringe head of the type defined at the outset above, the problem also arises that if the guard cap is unintentionally twisted the wrong direction relative to the anchoring element, the rated breaking point will indeed break but the cannula will now be forced through the sealing disk and put into communication with the medication contained in the syringe barrel.

SUMMARY OF THE INVENTION

The object of the invention is to create a hypodermic syringe head which in conjunction with conventional syringe barrels forms a ready-to-use syringe that can not only be constructed simply and under sterile conditions and provided with a tamper-evident closure, but also in which provisions are taken to prevent mistakes in use with the deleterious effects described.

The subject of the invention is a hypodermic syringe head with a tamper-evident closure for a syringe barrel, which has a barrel neck that is provided with an axial fluid outlet conduit and a circumferential bead for anchoring the hypodermic syringe head, having an injection cannula, which is mounted in a cannula carrier from which it protrudes on both axial ends and which is disposed in a cannula carrier guide so as to be movable relative thereto, and a cannula guard cap which is adjoined, via a rated breaking point, by an anchoring element that solidly holds the cannula carrier guide and can be affixed with elastic deformation to the circumferential bead of the barrel neck, and the cannula guard cap has axially extending ribs on its inside circumference which engage corresponding ribs of the cannula carrier for rotationally driving it, wherein embodied on the circumference of the cannula carrier are two axially symmetrical guide grooves for a guide peg, provided in the interior of the cannula carrier guide, which extend with a predetermined inclination substantially in a V and open into one another on their end oriented toward the sealing disk, and the guide peg, in the unactuated state of the hypodermic syringe head, engages the orifice region, oriented toward the sealing disk, of the guide grooves and upon a rotation of the cannula guard cap in each of the two directions of rotation slides relative to one of the two guide grooves, destroying the rated breaking point, so that the cannula carrier is rotated and moved together with the cannula relative to the sealing disk, wherein an axial introduction groove, open at the bottom, for the guide peg adjoins the orifice region, oriented toward the sealing disk, of the guide grooves and widens in the radial direction towards its inlet end, wherein the end of the injection cannula oriented toward the sealing disk is closed and is provided with a lateral opening, through which the medication can enter the cannula, after the syringe head has been activated, and wherein the sealing disk is pre-perforated, and in the unactuated state of the hypodermic syringe head the injection cannula closes the hole.

The hypodermic syringe head constructed according to the invention comprises only four separate parts, specifically the guard cap with the anchoring element, the sealing disk, the cannula carrier guide, and the cannula carrier with the cannula (glued together or high-frequency welded), and is therefore simple to produce and assemble. The guard cap joined to the anchoring element via a rated breaking point assures the temper-evident closure function. The cannula is integrated in protected fashion in the syringe head, and upon final assembly, the entire syringe head with all four separate parts is mounted as a unit on the syringe barrel, so that no damage to or contamination of the injection cannula whatever can occur. Once the syringe head has been mounted, the syringe barrel can be filled and equipped in sealed fashion with a suitable piston unit.

The activation of the injection is accomplished by twisting the guard cap, which breaks the rated breaking point and rotates the cannula carrier into the cannula carrier guide, specifically in an arbitrary direction of rotation. In the process, the cannula moves relative to the sealing disk, thus enabling the medication to enter the cannula. The guard cap is then twisted off in the axial direction, and the syringe is ready for injection.

The guide grooves according to the invention on the circumference of the cannula carrier guide assure that the guard cap, from its unactuated position, that is, while the rated breaking point is still intact, can be rotated in both rotational directions to actuate the syringe head, thus twisting the cannula carrier into the cannula carrier guide. This precludes twisting the guard cap by mistake, severing the rated breaking point, without putting the injection cannula into its operative position. At the same time, assembly is facilitated by the embodiment according to the invention of the guide groove.

It should be noted that from U.S. Pat. No. 5,250,037, a hypodermic syringe head is known in which guide grooves, extending substantially in a V on the circumference of the barrel neck are embodied for a guide peg provided in the interior of the cannula guard cap. The effect attained by this embodiment is that upon actuation of the guard cap in each of the two rotational directions, the cannula carrier pierces the sealing disk toward the barrel neck. However, the known construction has the disadvantage that first, because of how the guard cap is embodied, a germ-free closure is not obtained, of the kind achieved in the invention by snapping the guard cap onto the circumferential bead of the barrel neck, with elastic deformation and the defined rated breaking point. Nor is there any non-positive and positive drive of the cannula carrier in the reference, of the kind provided in the invention by the mutual rib engagement between the guard cap and the cannula carrier. In the construction of the invention, assembly is also made easier by the axial introduction groove for the guide peg, and moreover, because of the pre-perforated sealing disk that in the unactuated state is closed by the cannula, actuation is made easier, and the risk that sealing disk material will penetrate the cannula is also averted.

The embodiment according to the invention thus offers optimal freedom from germs, with reliable actuation in both rotational directions.

In a further characteristic of the invention, the inclination of the guide grooves is selected such that an approximately one-quarter rotation of the cannula carrier causes a travel of approximately 3 mm on the part of the cannula relative to the sealing disk. This travel distance assures that after an approximately one-quarter rotation, with simultaneous destruction of the tamper-evident closure of the cannula guard cap, the cannula will have passed so far through the sealing disk that the lateral inlet opening of the cannula is opened and the medication can be injected unhindered, once the already twisted-off cap has been removed.

Anchoring the hypodermic syringe head to the syringe barrel can be done by press-fitting or by a detent connection. The latter option is preferably employed, in which case the anchoring element is made of elastic material and is snapped onto the circumferential lead of the neck of the syringe barrel.

A further preferred characteristic of the invention is that the anchoring element is embodied conically on the inside, and the cannula carrier guide can be press-fitted into the anchoring part from the open end thereof. The press fit makes it easier and faster to assemble the ready-to-use syringe.

The assembly of the ready-to-use syringe can be further simplified if in accordance with a preferred characteristic of the invention, an annular groove for receiving the sealing disk during assembly is provided on the inside of the anchoring element. As a result, the hypodermic syringe head can be transported, sterilized, and stored in the fully assembled state before being mounted on prepared syringe barrel and piston units.

One essential advantage of the invention is that the medication does not come into contact with the interior of the cannula until the moment the ready-to-use syringe is activated, the temper-evident closure is twisted off, and the cannula guard cap is removed. This prevents the medication in the cannula, during the often very long-term storage of the syringes, from crystallizing out and thus also prevents the attendant stopping up of the cannula. Because of the described separation between the medication and the ready-to-use syringe closure system, sterility is also assured over a long period of time. The ready-to-use syringe therefore need not additionally be packed in sterile form after production but instead can be packed away in boxes without any additional wrapping over it.

BRIEF DESCRIPTION OF THE DRAWINGS

The invention will be described in further detail below in terms of an exemplary embodiment in conjunction with the drawings, in which.

DETAILED DESCRIPTION OF THE INVENTION

Figure 1:
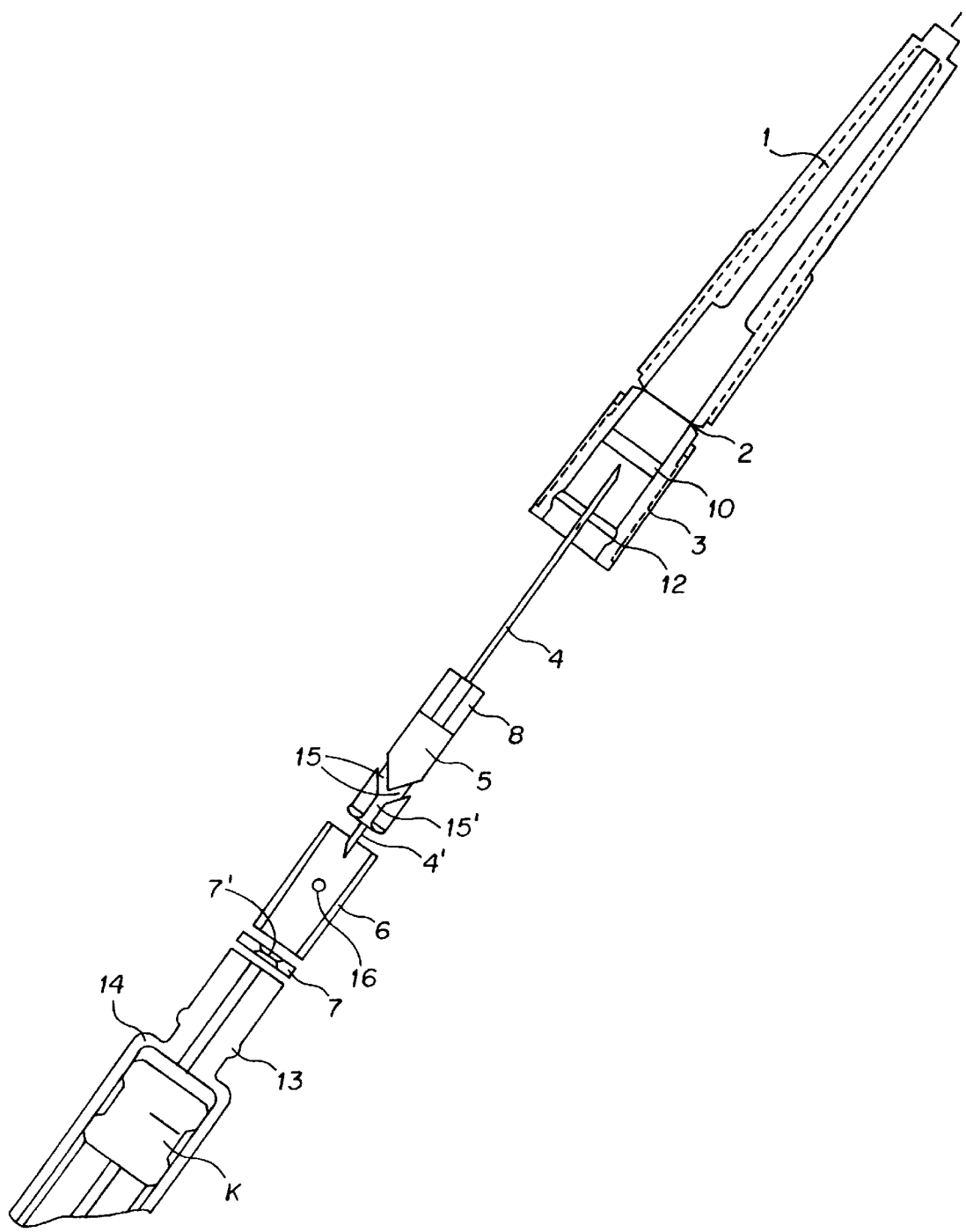
FIG. 1 is an exploded view of the hypodermic syringe head according to the invention in conjunction with a syringe barrel shown only in part.
Figures 2, 2A:
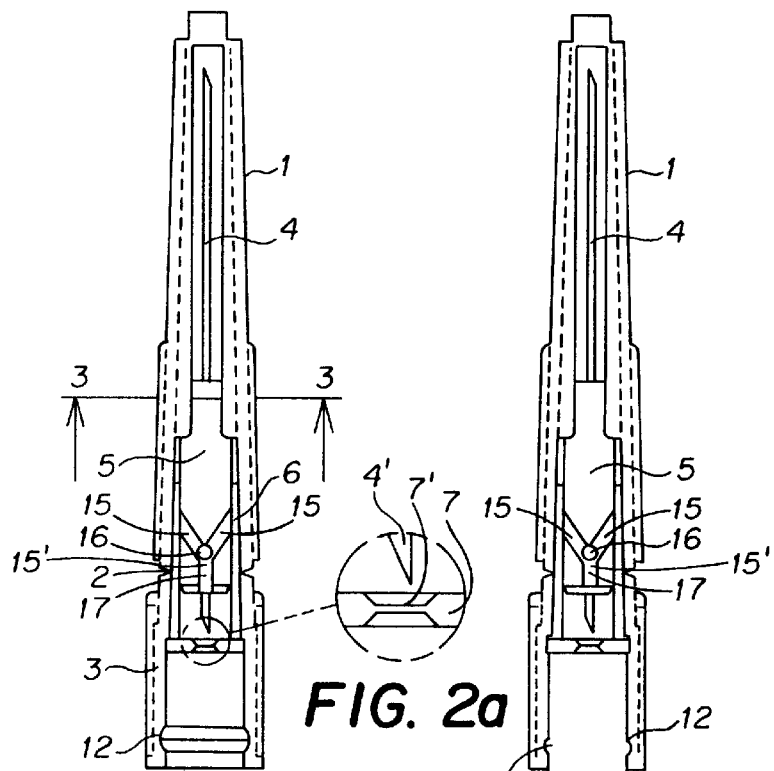
FIG. 2 is an axial section through an hypodermic syringe head according to the invention.
Figure 3:
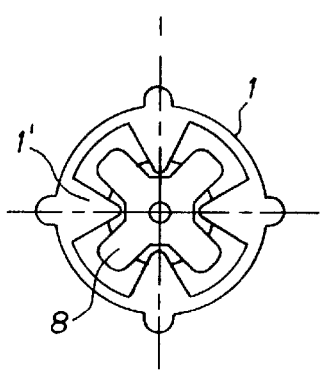
FIG. 3 is a section on a larger scale taken along the line 3—3 of FIG. 2.
Figure 4:
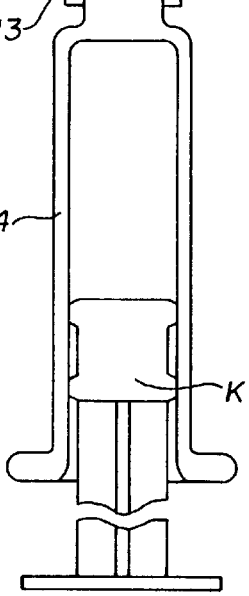
FIG. 4 is an axial section through the hypodermic syringe head of FIG. 1 in the assembled state.

The hypodermic syringe head of FIGS. 1 and 2 is composed essentially of four separate parts, specifically a guard cap 1, which is integrally joined via a rated breaking point 2 to an anchoring element 3; an injection cannula 4, which is solidly anchored in a cannula carrier 5, for instance by high-frequency welding or adhesive bonding; a cannula carrier guide 6; and a sealing disk 7. The cannula carrier 5 is cross-shaped in section, as shown in FIG. 3, with four ribs 8 between which radial ribs 1' of the cannula guard cap 1 protrude.

When the hypodermic syringe head is put together, the cannula carrier 5 is inserted far enough into the cannula carrier guide 6 that the end 4' of the cannula 4 protrudes out of the cannula carrier guide 6 on the side of the sealing disk 7. The cannula carrier guide 6 is then introduced into the anchoring element 3 and into the guard cap 1, from the free end thereof (FIG. 1), and by means of a conical embodiment of the outer circumference of the cannula carrier guide 6 and a corresponding conical embodiment of the inner wall of the anchoring element 3, an at least non-positive press fit is attained. In conclusion, the sealing disk 7 is inserted into the anchoring element 3 and snaps into an annular groove 10 on the inner circumference of the anchoring element 3. The hypodermic syringe head thus assembled in final form in this way is shown in FIG. 2 and can be transported, sterilized and stored without the risk of contamination of or damage to the injection cannula 4.

The sealing disk 7 shown in FIGS. 1 and 2 and 2a forms a diaphragm 7' in its central region.

Figures 6, 6A:
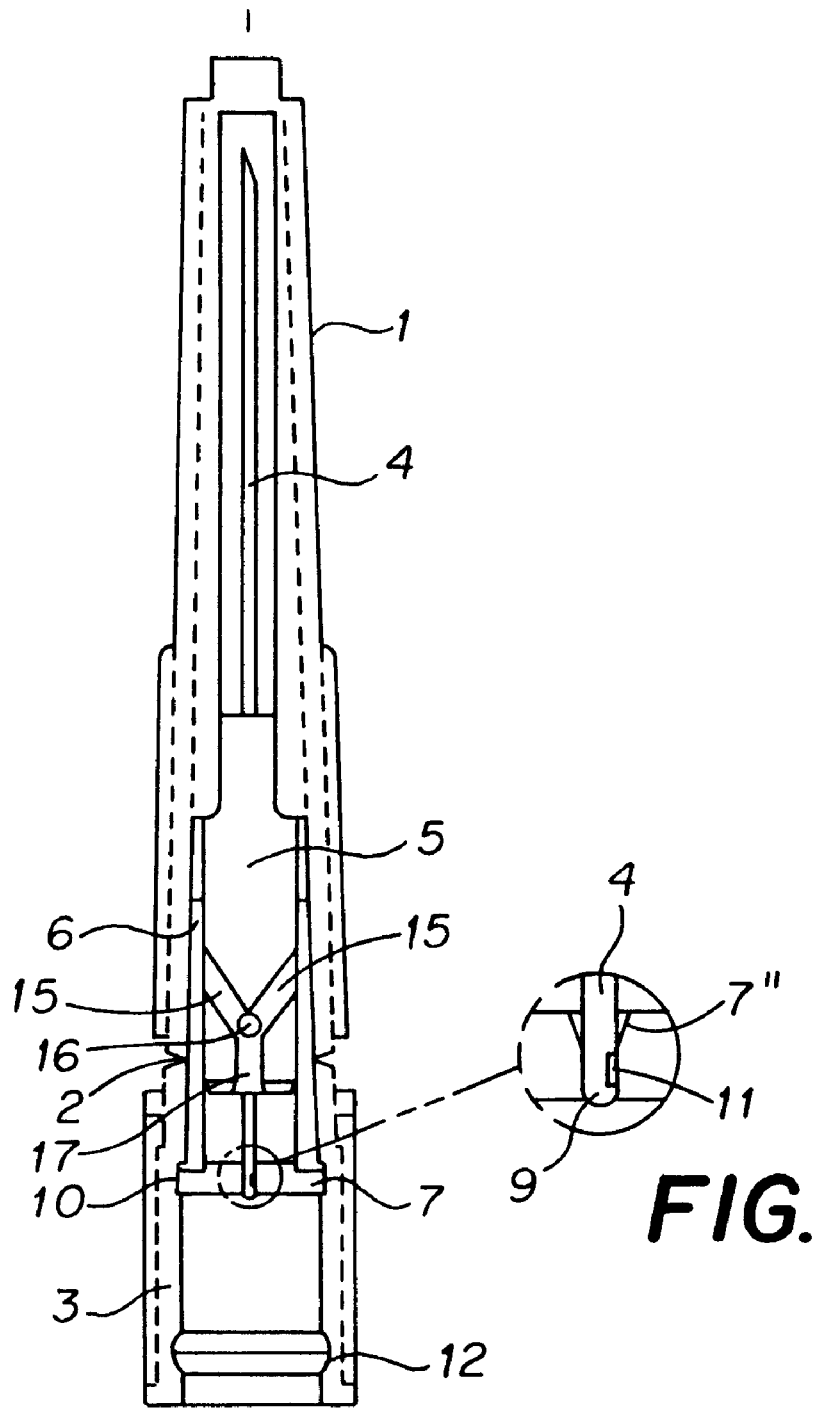
FIG. 6 is an axial section through a further exemplary embodiment of the hypodermic syringe head.

The end 4' of the injection cannula 4 toward the sealing disk 7 is sharpened or, as shown in FIG. 6, closed and provided with a lateral opening 11. In the first case, the injection cannula cooperates with a sealing disk 7, which in its central region is provided with a diaphragm 7' that is pierced by the cannula when the syringe is activated. In the case of the embodiment of FIG. 6, the sealing disk 7 is pre-perforated, and the closed end of the cannula closes the hole 7", which widens conically toward the top, before the syringe is activated. The anchoring element 3 is made of elastic material and can be snapped, with a circumferential groove 12, onto a circumferential lead 13 of the barrel neck of the syringe barrel 14. Alternatively, the anchoring element 3 could be press-fitted onto the barrel neck of the syringe barrel 14 or formed onto it by ultrasonic or high-frequency deformation. The syringe barrel 14 is filled with a medication and sealed off by the insertion of a piston unit K. The hypodermic syringe arrangement thus fully assembled is now ready for use.

Figure 5:
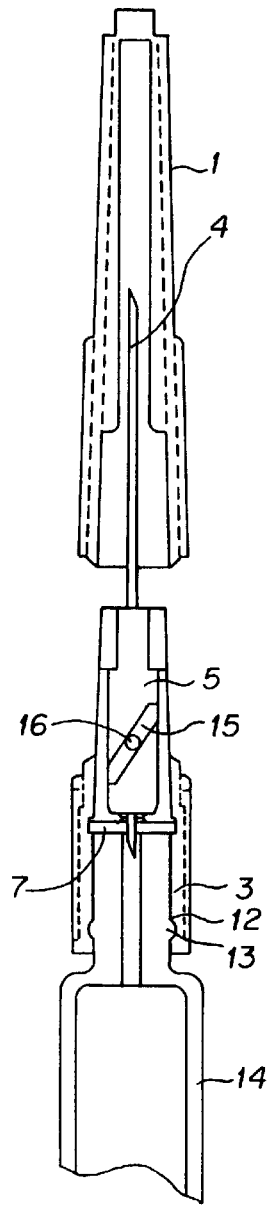
FIG. 5 shows the hypodermic syringe head of FIG. 4 after actuation.

To initiate the injection process, the cannula carrier 5 with the injection cannula 4 is twisted, by twisting off the guard cap 1, into the cannula carrier guide 6 in an arbitrary direction in such a way that in FIGS. 1–5 the sealing disk 7 is pierced, or in FIG. 6 the opening 11 of the cannula 4 has passed through the sealing disk 7 sufficiently to reach the region of the liquid medication. For the rotational operation of the cannula carrier 5 required for this purpose, the guard cap 1 is provided on its inner circumference with the four ribs 1', which engage the grooves of the cannula carrier or fit between the arms 8 thereof (FIG. 3). By twisting the guard cap 1 relative to the anchoring element 3, after the rated breaking point 2 has broken, a rotational drive of the cannula carrier 5 and thus, in FIGS. 1–5, piercing of the sealing disk 7 are brought about. The position achieved is shown in FIG. 5. In the embodiment in FIG. 6, the end 9 of the cannula, provided with the lateral opening 11, is moved out of the position shown in FIG. 6 into the syringe barrel chamber.

The cannula carrier 5, on its circumference, has two guide grooves 15, which extend axially symmetrically with predetermined inclination substantially to form a V. The guide grooves 15 open into one another at their end toward the sealing disk 7. The orifice region 15' oriented toward the sealing disk 7 is engaged by a guide peg 16 of the cannula carrier guide 6; when the cannula carrier and cannula carrier guide are put together, this guide peg is introduced into the orifice region 15' via an introduction groove 17 of the cannula carrier, which groove widens radially toward its inlet end. Rotating the guard cap 1 clockwise or counterclockwise in this way causes the end 4' of the injection cannula 4 to pass through the sealing disk 7, or causes the end 9 of the cannula to enter the syringe barrel. The inclination of the guide grooves 15 is selected such that with a one-quarter rotation of the cannula carrier 5, for instance, a travel of the cannula 4 of 3 mm, for example, relative to the sealing disk 7 is attained. This distance suffices for the cannula guard cap 1 to be twisted off the anchoring element 3 and for the sealing disk 7 to have been reliably passed so that the medication can enter the void of the cannula through the central opening or the lateral opening 11 of the cannula 4 and be injected.

It will be understood that the embodiment shown, with four ribs 1' or arms 8, is merely an example. Any arbitrary number of ribs, which enable an engagement fixed against relative rotation between the guard cap 1 and the cannula carrier 5, can be employed.

The guard cap 1, the anchoring element 3, cannula carrier 5 and cannula carrier guide 6 are preferably plastic parts made by injection molding.

I claim:

1. A hypodermic syringe head with a tamper-evident closure for a syringe barrel (14), which has a barrel neck that is provided with an axial fluid outlet conduit and a circumferential bead (13) for anchoring the hypodermic syringe head, having an injection cannula (4), which is mounted in a cannula carrier (5) from which it protrudes on both axial ends and which is disposed in a cannula carrier guide (6) so as to be movable relative thereto, and a cannula guard cap (1) which is adjoined, via a rated breaking point, by an anchoring element (3) that solidly holds the cannula carrier guide (6) and can be affixed with elastic deformation to the circumferential bead (12) of the barrel neck, wherein the cannula guard cap (1) has axially extending ribs (1') on its inside circumference which engage corresponding ribs (8) of the cannula carrier (5) for rotationally driving it, wherein embodied on the circumference of the cannula carrier (5) are two axially symmetrical guide grooves (15) for a guide peg (16), provided in the interior of the cannula carrier guide (6), which extend with a predetermined inclination substantially in a V and open into one another on their end oriented toward the sealing disk (7), and the guide peg, in the unactuated state of the hypodermic syringe head, engages the orifice region (15'), oriented toward the sealing disk (7), of the guide grooves (15) and upon a rotation of the cannula guard cap (1) in each of the two directions of rotation slides relative to one of the two guide grooves, destroying the rated breaking point (2), so that the cannula carrier is rotated and moved together with the cannula (4) relative to the sealing disk (7), wherein an axial introduction groove (17), open at the bottom, for the guide peg (16) adjoins the orifice region (15'), oriented toward the sealing disk (7), of the guide grooves (15) and widens in the radial direction towards its inlet end, wherein the end (9) of the injection cannula (4) oriented toward the sealing disk (7) is closed and is provided with a lateral opening (11), through which the medication can enter the cannula, after the syringe head has been activated, and wherein the sealing disk (7') is pre-perforated, and in the unactuated state of the hypodermic syringe head the injection cannula (4) closes the hole.

2. The hypodermic syringe head of claim 1, characterized in that the inclination of the guide grooves (15) is selected such that an approximately one-quarter rotation of the cannula carrier (5) causes a travel of approximately 3 mm on the part of the cannula (4) relative to the sealing disk (7).

3. The hypodermic syringe head of claim 2, characterized in that the anchoring element (3) is embodied conically on the inside, and the cannula carrier guide (6) can be press-fitted into the anchoring part (3) from the open end thereof.

4. The hypodermic syringe head of claim 3, characterized in that an annular groove (10) for receiving the sealing disk (7, 7') is provided on the inside of the anchoring element (3).

5. The hypodermic syringe head of claim 1, characterized in that the anchoring element (3) is embodied conically on the inside, and the cannula carrier guide (6) can be press-fitted into the anchoring part (3) from the open end thereof.

6. The hypodermic syringe head of claim 5, characterized in that an annular groove (10) for receiving the sealing disk (7, 7') is provided on the inside of the anchoring element (3).

7. The hypodermic syringe head of claim 1, characterized in that an annular groove (10) for receiving the sealing disk (7, 7') is provided on the inside of the anchoring element (3).

8. The hypodermic syringe head of claim 2, characterized in that an annular groove (10) for receiving the sealing disk (7, 7') is provided on the inside of the anchoring element (3).

* * * * *